United States Patent [19]

Coakley et al.

[11] Patent Number: 5,665,605
[45] Date of Patent: Sep. 9, 1997

[54] PARTICLE AGGREGATION METHOD AND APPARATUS

[75] Inventors: William Terence Coakley, Cardiff; Martin Alan Grundy, Pembroke Dock, both of United Kingdom; Werner Bolex, Vienna, Austria

[73] Assignee: University College Cardiff Consultants Limited, United Kingdom

[21] Appl. No.: 302,658

[22] PCT Filed: Mar. 10, 1993

[86] PCT No.: PCT/GB93/00504

§ 371 Date: Sep. 8, 1994

§ 102(e) Date: Sep. 8, 1994

[87] PCT Pub. No.: WO93/19367

PCT Pub. Date: Sep. 30, 1993

[30] Foreign Application Priority Data

Mar. 10, 1992 [GB] United Kingdom ............... 9205128

[51] Int. Cl.$^6$ .......................... G01N 33/557; G01N 1/18
[52] U.S. Cl. ............... 436/174; 436/514; 436/517; 436/536; 436/539; 435/287.2; 435/288.1; 422/73
[58] Field of Search ................ 436/174, 501, 436/503, 514, 517, 519, 536, 538, 539; 435/7.1, 7.2, 7.25, 296, 315

[56] References Cited

U.S. PATENT DOCUMENTS

| 4,615,984 | 10/1986 | Stoker | 436/518 |
|---|---|---|---|
| 4,795,698 | 1/1989 | Owen et al. | 435/4 |
| 5,164,094 | 11/1992 | Stuckart | 210/708 |
| 5,227,312 | 7/1993 | Grundy | 436/517 |

FOREIGN PATENT DOCUMENTS

| 508675 | 6/1939 | United Kingdom. |
|---|---|---|
| 2-233-089 | 1/1991 | United Kingdom. |
| 2233089 | 1/1991 | United Kingdom. |
| WO 88/04051 | 6/1988 | WIPO. |
| WO 88/09210 | 12/1988 | WIPO. |

OTHER PUBLICATIONS

Jepras et al., "Agglutination of *Legionella pneumophila* by antiserum is accelerated in an ultrasonic standing wave", *Journal of Immunological Methods*, 120, pp. 201–205 (1989).

Dyson et al., "Segregation and Sedimentation of red Blood Cells in Ultrasonic Standing Waves", *Nature*, 239, pp. 398–399 (1972).

Whitworth et al., "Transport and harvesting of suspended particles using modulated ultrasound", *Ultrasonics*, 29, pp. 439–444 (1991).

*Primary Examiner*—Harold Pyon
*Attorney, Agent, or Firm*—Schwegman, Lundberg, Woessner & Kluth, P.A.

[57] ABSTRACT

A sample of liquid with suspended particles is contained in a tube and subjected to a standing wave ultrasound field transverse to the tube, the standing wave exhibiting a progressive change in pressure amplitude transverse to the tube, so that particles in suspension are displaced transversely of the tube to one or more predetermined regions; exposure of the sample to the standing wave is then terminated and the particles are allowed to settle, and inspected to determine whether they remain aggregated or whether they dissociate. The ultrasound field is produced by a transducer of tubular form encircling the tube. The invention may be used for agglutination of particles or cells via cross-bridging molecules in immuno-agglutination assays.

10 Claims, 2 Drawing Sheets

PARTICLE AGGREGATION METHOD AND APPARATUS

FIELD OF THE INVENTION

This invention relates to a method and apparatus for the aggregation of particles, more particularly for the agglutination of particles via cross-bridging molecules as occurs for example in immuno-agglutination assays, where cross-bridging is via antibody molecules.

BACKGROUND OF THE INVENTION

GB 2 233 089 discloses a method and apparatus for monitoring the aggregation of particles suspended in a liquid, in which a sample of the liquid is subjected to ultrasound to promote aggregation and possible agglutination of particles, and then the particles are allowed to settle onto a meniscus of the sample. A visual inspection of the particles once settled on the meniscus enables a determination of whether an agglutination reaction has occurred: agglutinated cells lie in clumps distributed over the meniscus whereas clumps of non-agglutinated particles dissociate and form a ring around the edge of the meniscus.

The method and apparatus disclose-in GB 2 233 089 is particularly applicable to the detection of Hepatitis B virus, a reaction mixture being formed of a serum sample plus a suspension of appropriate erythrocytes coated with antibody to Hepatitis B surface antigen. Viral agglutination of the erythrocytes gives a positive test reaction.

In GB 2 233 089, ultrasound is coupled via a reservoir into the bottom of a vertical capillary tube containing the sample. The arrangement is not suited to multiple-sample testing because the reservoir, in which the capillary tube stands, must be washed out and refilled for each test; also continuous movement of successive samples through the capillary tube is impractical because the ultrasonic transducer is positioned across one end of the capillary tube.

SUMMARY OF THE INVENTION

We have now devised an improved method and apparatus for rapid aggregation of particles.

In accordance with this invention, there is provided a method for the aggregation of particles suspended in a liquid, comprising containing a sample S of the liquid in a tube, generating a standing wave ultrasound field transverse to the tube, the standing wave exhibiting a progressive change in pressure amplitude transverse to the tube, so that particles in suspension are displaced transversely of the tube to one more predetermined regions, and then terminating the exposure of the sample S to the standing wave and allowing the particles to settle.

Once the particles have settled, they are inspected to determine whether they have remained aggregated or whether they have dissociated. Alternatively, or in addition, the particles can be inspected whilst they are in the process of settling. In any event, the inspection can be carried out by the eye, or by directing a beam of light at the particles and using a sensor to respond to the reflected or transmitted beam.

Preferably the standing wave exhibits a progressive change in pressure amplitude from a first region within the tube to said predetermined region or regions, which are spaced inwards from the inner surface of the tube but preferably are closer to the inner surface than said first region. For example the standing wave may exhibit a pressure amplitude maximum at or adjacent a longitudinal axis of the tube and a pressure amplitude minimum at a said predetermined region spaced inwards from the inner surface of the tube.

Preferably the ultrasound standing wave field extends radially outwards from a longitudinal axis of the tube in different angular directions, and preferably in all angular directions through 360°. Preferably the ultrasound standing wave field is generated by a transducer of tubular form which encircles the tube containing the liquid sample S.

Preferably the sample S of liquid has an upper boundary U and a meniscus at its lower boundary L within the tube, and the particles are allowed to settle onto this meniscus.

The arrangement enables the sample tube to contain several liquid samples S, separated by bubbles of air or other fluid, so that the sample tube can be displaced longitudinally, taking the successive samples through the ultrasound field and then into a position where the particles can settle. Instead, successive samples S separated by bubbles of air or other fluid can be caused to flow through the sample tube.

Also in accordance with this invention, there is provided an apparatus for the aggregation of particles, comprising a tube for containing a liquid S and an ultrasonic transducer arranged to generate a standing wave ultrasound field transverse to the tube, the standing wave exhibiting a progressive change in pressure amplitude transverse to the tube, so that, in use of the apparatus, particles in suspension are displaced transversely of the tube to one or more predetermined regions.

The tube may be disposed generally vertically so that the particles will settle onto the lower meniscus of the liquid sample. Instead, the tube may be inclined at an angle to the vertical, so that the particles settle onto a side wall of the tube and/or into a corner C between the side wall and the meniscus.

BRIEF DESCRIPTION OF THE DRAWINGS

Embodiments of this invention will now be described by way of examples only and with reference to the accompanying drawings, in which.

DESCRIPTION OF THE PREFERRED EMBODIMENTS

Figure 1:
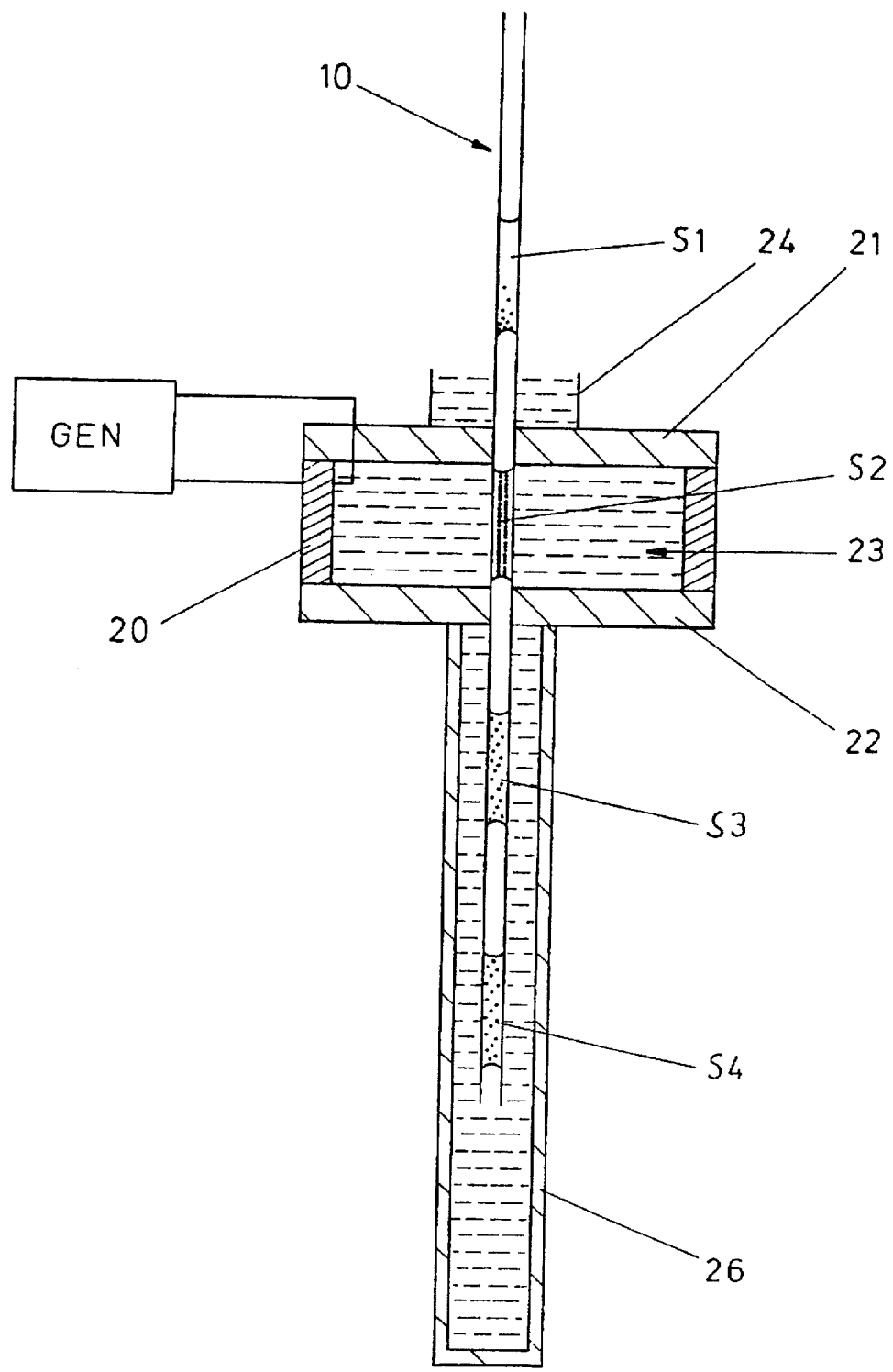
FIG. 1 is a schematic vertical section through an apparatus for performing an immuno-agglutination assay in accordance with the invention.

Referring to FIG. 1 of the drawing, there is shown a vertically-disposed glass capillary tube 10 containing a number of samples S1 to S4 separated by air spaces. A piezoelectric ultrasonic transducer 20, of circular-section tubular shape, encircles the capillary tube coaxially. Two discs 21,22 of e.g. perspex are sealed across the top and bottom of the transducer to form a housing 23 which is filled with water. The capillary tube 10 passes in a close-fit manner through holes in the centres of the discs 21,22. An elongate tube 26 is sealed to the underside of the lower disc 22 and is also filled with water. A reservoir 24 of water is provided on the top of the upper disc 21 and serves to prevent air being introduced into the housing 23 during displacement of the capillary tube 10.

The transducer 20 is provided with electrodes over its inner and outer surfaces and an a.c. generator GEN is connected across these electrodes to drive the transducer in its thickness mode. Accordingly, a standing wave ultrasound field is generated, extending radially outwards in all angular directions from the longitudinal axis of the capillary tube 10. The standing wave exhibits a primary pressure amplitude maximum substantially on the axis of the capillary tube, and successive maxima, of lower amplitude, at half-wavelength intervals radially outwards from the tube axis. The frequency of the a.c. excitation signal is selected, having regard to the internal diameter of the capillary tube, so that the first pressure amplitude minimum lies at a position spaced radially inwards from the inner surface of the capillary tube. Thus in use, particles in the liquid sample B, which is disposed in the ultrasound field, are displaced to an annular region at the position of the first pressure amplitude minimum.

The ultrasound field thus causes aggregation of the particles at the annular region of the first pressure amplitude minimum and furthermore promotes any possible agglutination.

In use, a number of liquid sample S are contained within the capillary tube separated by the spaces filled with air or other fluid each sample S including, for example when testing for Hepatitis B virus in blood, serum and a suspension of appropriate erythrocytes coated with antibody to Hepatitis B surface antigen. Agglutination is promoted by the ultrasound field in the case of a positive sample, when the serum contains Hepatitis B virus. The capillary tube 10 is inserted until the top sample lies within the transducer housing 23, and the a.c. drive signal is connected to the transducer for e.g. 15 seconds. After this, the capillary tube is slid upwards until the second-from-top sample lies within the transducer housing 23, and the transducer is switched on for another e.g. 15 second period. The particles in the top sample are now able to settle under gravity onto the lower meniscus of this sample, and the meniscus can be observed. As mentioned above, if agglutination occurs, the meniscus exhibits a granular appearance with groups or clumps of particles spread over the meniscus surface, otherwise the clumps of particles or cells disperse or disaggregate as they settle and form a smooth or uniform ring around the edge of the meniscus. Thus, visual inspection shows whether the test has proved positive or negative.

It will be appreciated that the method which has been described enables several samples to be contained within a single capillary tube and tested one-after-another. The stepwise displacement of the capillary tube may be effected manually or automatically. In a modification, it is possible to cause successive samples S separated by gaps of air or other fluid, to flow through a fixed capillary tube disposed on the axis of the ultrasound transducer.

Figure 2:
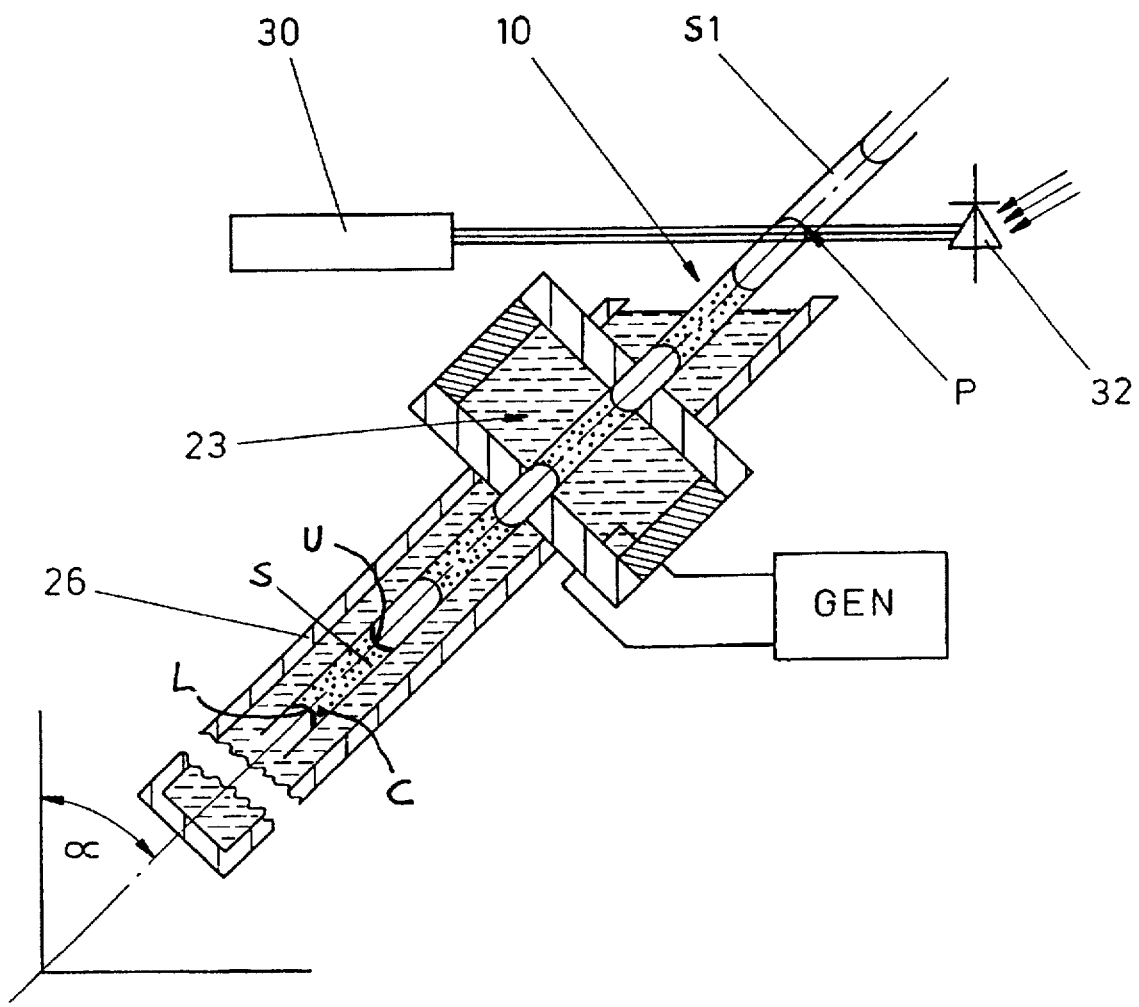
FIG. 2 is a similar section through a modified apparatus in accordance with the invention.

Whilst the use of a capillary tube in a generally vertical disposition has been described, the capillary tube may instead be inclined at an angle to the vertical, as shown in FIG. 2. The particles will then settle under gravity onto the side wall of the tube and/or into the corner C between the tube wall and the meniscus, as shown at P. The particles can then be inspected at the location(s) where they have settled: as mentioned previously, inspection may be carried out by directing a beam of light (e.g. from a laser 30) at the particles and using a sensor e.g. 32 to pick up the transmitted beam.

Also, whilst the method and apparatus have been described with reference to the agglutination of particles or cells via cross-bridging molecules, the method and apparatus are applicable to other uses where it is desired to test the extent to which particles link or bond together when aggregated, e.g. in the case of flocculation. However, it will be appreciated that in all of the cases which have been described, the nature of the particles is such that they do not bond or adhere to the inner surface of the tube, should they come into contact with that surface, but instead they slide down that surface when allowed to settle under gravity upon removing the ultrasonic field.

Further, whilst the method and apparatus have been described as using an ultrasonic transducer of tubular form encircling the sample tube, transducers of other forms may be envisage, e.g. a planar transducer, to provide a standing wave ultrasound field transverse to the tube.

We claim:

1. A method of carrying out an immuno-agglutination assay, the method comprising:

providing a sample of liquid in which particles potentially susceptible to agglutination are suspended;

containing said sample within a tube in a manner producing an upper and a lower boundary on said liquid sample within the tube, said lower boundary forming a meniscus onto which said particles are allowed to settle;

placing said tube such that it is encircled by a tubular ultrasound transducer;

exciting said tubular ultrasound transducer to generate a standing wave ultrasound field within said tube, said standing wave field extending radially of said tube and exhibiting a progressive change in pressure amplitude radially within said tube so that particles suspended in said liquid sample are displaced radially of said tube to aggregate at least one predetermined annular region;

terminating the exposure of said liquid sample to said standing wave and allowing said particles to settle; and inspecting said particles whilst said particles are settling to determine whether they remain aggregated together or whether they disperse.

2. A method as claimed in claim 1, further including the step of inclining said tube to a vertical position whereby said particles are allowed to settle onto an inner side surface of said tube.

3. A method as claimed in claim 1, whereby said particles are allowed to settle into a corner between an inner side surface of said tube and said meniscus.

4. A method as claimed in claim 1, in which the step of generating said standing wave field exhibits a progressive change in pressure amplitude from a first region within said tube to said at least one predetermined annular region, said at least one predetermined annular region being spaced inwards from an inner surface of said tube but closer than said first region to said inner surface.

5. A method as claimed in claim 1, in which the step of generating said standing wave field exhibits a primary pressure amplitude maximum substantially on a longitudinal axis of said tube and successive maxima, or lower amplitude, at half wavelength intervals radially outwards from said axis of said tube.

6. A method as claimed in claim 1, further including the steps of providing a plurality of said liquid samples, containing said liquid samples in said tube separated by bubbles of air or other fluid and successively stepping said liquid samples, longitudinally of said tube, through said ultrasound standing wave field.

7. A method of carrying out an immuno-agglutination assay, the method comprising:

providing a sample of liquid in which particles potentially susceptible to agglutination are suspended;

containing said sample within a tube in a manner producing an upper and a lower boundary on said liquid sample within the tube, said lower boundary forming a meniscus onto which said particles are allowed to settle;

placing said tube such that it is encircled by a tubular ultrasound transducer;

exciting said tubular ultrasound transducer to generate a standing wave ultrasound field within said tube, said standing wave field extending radially of said tube and exhibiting a progressive change in pressure amplitude radially within said tube so that particles suspended in said liquid sample are displaced radially of said tube to aggregate at least one predetermined annular region;

terminating the exposure of said liquid sample to said standing wave and allowing said particles to settle; and inspecting said particles is carried out once said particles have settled.

8. An apparatus for carrying out an immuno-agglutination assay, said apparatus comprising:

a tube for containing a liquid sample in which particles potentially susceptible to agglutination are suspended;

said tube being inclined to the vertical so that said particles will, in use of the apparatus, settle onto an inner side surface of said tube and/or into a corner between said inner side surface and a meniscus at a lower boundary of said liquid sample;

a tubular ultrasound transducer positioned to encircle said tube;

means to excite said tubular ultrasound transducer to generate a standing wave ultrasound field within said tube, said standing wave field extending radially of said tube and exhibiting a progressive change in pressure amplitude radially within said tube so that, in use of said apparatus, said particles suspended in said liquid sample are displaced radially of said tube to aggregate at least one predetermined annular region; and means to inspect said particles whilst said particles are settling to determine whether they remain aggregated or whether they disperse.

9. An apparatus as claimed in claim 8, in which said tube is disposed vertically so that said particles will, in use of the apparatus, settle onto a meniscus at a lower boundary of said liquid sample.

10. An apparatus as claimed in claim 8, arranged so that, in use, said standing wave field exhibits a primary pressure amplitude maximum substantially on a longitudinal axis of said tube, and successive maxima, of lower amplitude, at half-wavelength intervals radially outwards from said axis of said tube.

* * * * *

UNITED STATES PATENT AND TRADEMARK OFFICE
CERTIFICATE OF CORRECTION

PATENT NO. : 5,665,605
DATED : September 9, 1997
INVENTOR(S) : William Terence Coakley et al.

It is certified that error appears in the above-identified patent and that said Letters Patent is hereby corrected as shown below:

At Col. 2, line 23, please delete "a liquid S" and insert --a liquid sample S--.

At Col. 3, line 11, please delete "sample B," and insert --sample S,--.

At Col. 3, line 19, please delete "liquid sample" and insert --liquid samples--.

At Col. 3, line 47, please delete "samples S separated" and insert --samples S, separated--.

Signed and Sealed this

Third Day of August, 1999

Attest:

Q. TODD DICKINSON

*Attesting Officer*       *Acting Commissioner of Patents and Trademarks*